United States Patent
Minnucci et al.

(10) Patent No.: US 11,827,923 B2
(45) Date of Patent: Nov. 28, 2023

(54) METHOD OF FLUORESCENT DETECTION OF ISOTHERMAL LOOP-MEDIATED AMPLIFICATION (LAMP) OF A TARGET NUCLEIC ACID, OLIGONUCLEOTIDES AND KITS THEREOF

(71) Applicant: DIASORIN S.p.A., Saluggia (IT)

(72) Inventors: Giulia Minnucci, Settimo Milanese (IT); Riccardo Mesturini, Rho (IT)

(73) Assignee: DIASORIN S.p.A., Saluggia (IT)

( * ) Notice: Subject to any disclaimer, the term of this patent is extended or adjusted under 35 U.S.C. 154(b) by 274 days.

(21) Appl. No.: 17/226,475

(22) Filed: Apr. 9, 2021

(65) Prior Publication Data

US 2021/0230682 A1    Jul. 29, 2021

Related U.S. Application Data

(62) Division of application No. 16/061,991, filed as application No. PCT/EP2016/081673 on Dec. 19, 2016, now Pat. No. 10,982,270.

(30) Foreign Application Priority Data

Dec. 22, 2015 (IT) ................ 102015000086668

(51) Int. Cl.
  C12Q 1/6844   (2018.01)
  C12Q 1/6853   (2018.01)

(52) U.S. Cl.
CPC ......... *C12Q 1/6844* (2013.01); *C12Q 1/6853* (2013.01); *C12Q 2525/161* (2013.01); *C12Q 2525/301* (2013.01); *C12Q 2527/101* (2013.01); *C12Q 2531/119* (2013.01); *C12Q 2565/101* (2013.01)

(58) Field of Classification Search
CPC .. C12Q 1/6844; C12Q 1/6853; C12Q 1/6818; C12Q 2525/161; C12Q 2525/301; C12Q 2527/101; C12Q 2531/119; C12Q 2565/101

See application file for complete search history.

(56) References Cited

U.S. PATENT DOCUMENTS

| | | | |
|---|---|---|---|
| 10,724,091 B1 | 7/2020 | Meagher et al. | |
| 10,982,270 B2 * | 4/2021 | Minnucci | C12Q 1/6844 |
| 2013/0171643 A1 | 7/2013 | Kubota et al. | |
| 2016/0053309 A1 | 2/2016 | Kitani et al. | |

FOREIGN PATENT DOCUMENTS

| WO | WO 2011/163425 | 12/2011 |
|---|---|---|
| WO | WO 2014/157377 | 10/2014 |
| WO | WO 2015/127201 | 8/2015 |
| WO | WO 2017/108663 | 6/2017 |

OTHER PUBLICATIONS

Chen, Q. et al. (1997) "Fluorescence Resonance Energy Transfer Study of Shape Changes in Membrane-Bound Bovine Prothrombin and Meizothrombin," Biochemistry 36(15):4701-11.
Chou, P.-H. et al. (2011) "Real-Time Target-Specific Detection Of Loop-Mediated Isothermal Amplification For White Spot Syndrome Virus Using Fluorescence Energy Transfer-Based Probes," J. Virol. Methods. 173(1):67-74.
Clegg, R.M. (1995) "Fluorescence Resonance Energy Transfer," Curr. Opin. Biotechnol. 6:103-110.
Eiken website (loop) http://loopamp.eiken.co.jp/e/lamp/loop.html (2005) 2 pages.
Eiken website (primer) http://loopamp.eiken.co.jp/e/lamp/primer.html (2005) 2 pages.
Gandelman, O.A. et al.( 2010) "Novel Bioluminescent Quantitative Detection of Nucleic Acid Amplification in Real-Time," PLoS One 5(11): e14155 (pp. 1-13).
International Search Report PCT/EP2016/081673 (2017) 6 pages.
Le Reste, L. et al. (2012) "Characterization of Dark Quencher Chromophores as Nonfluorescent Acceptors for Single-Molecule FRET," Biophysical J. 102:2658-2668.
Mair, G. et al. (2013) "Isothermal Loop-Mediated Amplification (LAMP) for Diagnosis of Contagious Bovine Pleuro-Pneumonia," BMC Veterinary Research 9:108 (pp. 1-8).
Mori, Y. et al. (2001) "Detection of Loop-Mediated Isothermal Amplification Reaction by Turbidity Derived From Magnesium Pyrophosphate Formation," Biochem. Biophys. Res. Commun. 289:150-154.
Notomi, T. et al (2000) "Loop-Mediated Isothermal Amplification of DNA," Nucleic acids Res. vol. 28(12)-e63 (pp. 1-7).
Tomita, N. et al. (2008) "Loop-Mediated Isothermal Amplification (LAMP) Of Gene Sequences And Simple Visual Detection Of Products," Nat. Protoc. 3:877-882.
Written Opinion PCT/EP2016/081673 (2017) 6 pages.
Zerilli, F. et al. (2010) "Methylation-Specific Loop-Mediated Isothermal Amplification for Detecting Hypermethylated DNA in Simplex and Multiplex Formats," Clin. Chem. 56:1287-1296.
Zhang, X. et al. (2013) "Development of a Real-Time Fluorescence Loop-Mediated Isothermal Amplification Assay for Rapid and Quantitative Detection of Fusarium oxysporum f. sp. Cubense Tropical Race 4 In Soil," PLoS One 8(12):e82841 (pp. 1-10).

* cited by examiner

*Primary Examiner* — David C Thomas
(74) *Attorney, Agent, or Firm* — STERNE, KESSLER, GOLDSTEIN & FOX

(57) ABSTRACT

The invention concerns a method for detecting isothermal loop-mediated (LAMP) amplification of a target nucleic acid sequence which is based on the fluorescence resonance energy transfer (FRET) mechanism. The invention also concerns a set of oligonucleotides and a kit adapted for carrying out the LAMP-FRET method of the invention.

20 Claims, 4 Drawing Sheets

Specification includes a Sequence Listing.

A. DiaSorin Strategy

B. Chou et al Strategy

A. FRET

B. Intercalating dye

METHOD OF FLUORESCENT DETECTION OF ISOTHERMAL LOOP-MEDIATED AMPLIFICATION (LAMP) OF A TARGET NUCLEIC ACID, OLIGONUCLEOTIDES AND KITS THEREOF

CROSS-REFERENCE TO RELATED APPLICATIONS

This application is divisional of, and claims priority to, U.S. patent application Ser. No. 16/061,991 (filed on Jun. 13, 2018; pending), which is a § 371 National Stage Application of PCT/EP2016/081673 (filed on Dec. 19, 2016; now lapsed), which application claims the benefit of IT Patent Application No. 102015000086668 (filed on Dec. 22, 2015). Each of these applications is hereby incorporated by reference in its entirety.

REFERENCE TO SEQUENCE LISTING

This application includes one or more Sequence Listings pursuant to 37 C.F.R. 1.821 et seq., which are disclosed in computer-readable media (file name: Sequence_Listing_PC1504EC.txt, created on Jun. 5, 2018, and having a size of 3,033 bytes), which file is herein incorporated by reference in its entirety.

FIELD OF THE INVENTION

The present invention relates to a method for detecting nucleic acid amplification by means of loop-mediated isothermal amplification (LAMP), as well as to a set of oligonucleotides and a kit for carrying out the method of the invention.

BACKGROUND OF THE INVENTION

Loop-mediated isothermal amplification (LAMP) is a recently developed method of nucleic acid amplification via an autocyclic strand displacement reaction, which is performed at a constant temperature, usually between 60° C. and 65° C. (Notomi T. et al 2000. Nucleic acids Res. Vol. 28(12)-e63). This technology employs a DNA polymerase with strand displacement activity and a set of four oligonucleotides, termed inner and outer primers, specifically designed to recognize six different recognition sites on the target nucleic acid. The two outer primers play a role in strand displacement during the non-cyclic step only whereas the inner primers include both sense and antisense sequences and contribute to formation of typical LAMP amplification products having stem-loop structures.

In addition to the four oligonucleotide primers, the LAMP assay may involve the use of two additional primers, the so-called loop primers, to improve amplification efficiency, thereby resulting in a total of six primers per target sequence. Such a combination of different primers, which span eight distinct sequences on the target nucleic acid, provides for a remarkable degree of assay specificity.

LAMP-based technology possesses the advantages of high sensitivity, rapid amplification, and simple operation. LAMP assay results in a highly efficient synthesis of amplified products, which is at least 50 times higher than the one obtained by classical PCR reactions in identical volumes. In addition, the ability to amplify nucleic acid under isothermal conditions enables the use of simple and cost-effective equipment, without the requirement of thermal cycling. In LAMP assays, both the amplification and detection of specific amplicons may be accomplished in a single step, thereby significantly decreasing the reaction time compared to a standard RT-PCR.

Several methods have been employed for the detection of LAMP amplification products including visual examination or turbidity monitoring of precipitated magnesium pyrophosphate (Tomita N., et al. 2008. Nat. Protoc. 3:877-882; Mori Y., et al. 2001. Biochem. Biophys. Res. Commun. 289:150-154), fluorescence detection of double-stranded DNA (dsDNA) with an intercalating fluorophore (Zhang X, et al. 2013, PLoS One 8(12):e82841; Mair G. et al. 2013, BMC Veterinary Research 9:108), bioluminescence reporting through pyrophosphate conversion (Gandelman O A., et al. 2010, PLoS One 5(11): e14155).

Known strategies for the indirect detection of LAMP amplification rely essentially on the formation of pyrophosphate as a reaction byproduct. As LAMP reactions proceed, pyrophosphate ions are released by incorporation of deoxynucleotide triphosphates (dNTPs) into the DNA strand during nucleic acid polymerization and these ions react with divalent metal ions, particularly magnesium ions, present in the reaction mix to produce a white, insoluble magnesium pyrophosphate precipitate (Mori Y., et al. 2001. Biochem. Biophys. Res. Commun. 289:150-154). This product results in a progressive increase in the turbidity of the reaction solution and pyrophosphate precipitates can be measured quantitatively in terms of turbidity or observed by the naked eye as a pellet after centrifugation. In an alternative format, the detection of LAMP amplification is achieved through the incorporation of manganese ions and calcein in the reaction. Calcein's fluorescence is naturally quenched by binding of manganese ions. Pyrophosphate production as a byproduct of LAMP reaction removes manganese ions form the buffer through precipitation, and the increased turbidity coupled with restored calcein fluorescence enables an easy visual read-out upon excitation with either visible or UV light (Tomita N., et al. 2008. Nat. Protoc. 3:877-882). In still another detection format, the enzymatic conversion of pyrophosphate into ATP, which is produced during DNA synthesis, is monitored through the bioluminescence generated by thermostable firefly luciferase (Gandelman O A., et al. 2010, PLoS One 5(11): e14155).

LAMP amplification products may also be detected through direct approaches which act via fluorescence reporting. The majority of such approaches are based on the use of intercalating dyes, such as ethidium bromide, SYBR Green, EvaGreen and YO-PRO-I (Zhang X, et al. 2013, PLoS One 8(12):e82841; Mair G. et al. 2013, BMC Veterinary Research 9:108). Typically, intercalating dyes are non-sequence-specific fluorescent dyes that exhibit a large increase in fluorescence emission upon binding into dsDNA. Such property may be used to monitor the nucleic acid amplification in real time by continuously measuring the fluorescence during the LAMP reaction. However, since intercalating dyes bind to any dsDNA, the implementation of such dyes in real-time amplification methods does not allow to discriminate between specific target amplification products and co-produced artifacts, such as non-specific amplicons and primer-dimers, which may result in an overestimation of the target concentration. Consequently, the detection of nucleic acid amplification by intercalating dyes requires extensive optimization and follow-up assays are usually needed to validate the results.

Fluorescence-based detection of LAMP amplification may also rely on the mechanism of Förster resonance energy transfer (FRET) (Chen Q, et al. 1997 Biochemistry 36(15): 4701-11). FRET is a distance-dependent interaction between the electronic excited states of two chromophores in which excitation energy is transferred from a donor molecule to an acceptor molecule. When the acceptor itself is a fluorophore, the FRET-induced acceptor excited state can subsequently relax by acceptor fluorescence emission. The acceptor chromophore does not need itself to be fluorescent, and FRET systems with dark acceptors have been largely implemented in recent years. For instance, dark quenchers may be used which are chromophores that can be excited to higher electronic states upon absorption of photons and relax to the ground state preferentially by nonradiative processes, thereby remaining dark (Le Reste L. et al. 2012. Biophysical Journal 102: 2658-2668). Acceptance of donor energy by a FRET acceptor requires that the absorbance spectrum of the acceptor chromophore overlaps with the emission spectrum of the donor chromophore. Further, the donor and acceptor chromophores need to be in close proximity for energy transfer to occur and the efficiency of such transfer is highly dependent on the sixth power of the distance between the two chromophores (Clegg R M. 1995 Curr. Opin. Biotechnol. 6: 103-110).

Chou et al. (Chou P H, et al. 2011 J Virol Methods. 173(1):67-74) describe an assay for the diagnosis of White spot syndrome virus (WSSV) infections in shrimps, which combines LAMP and FRET hybridization probe technology. More specifically, in addition to the standard set of LAMP primers, including the so-called loop-primers, the assay by Chou et al. involves the use of two fluorescent probes labeled at the 3'- and 5'-end sequence, respectively (FIG. 1A), which hybridize in a head to tail configuration to the single-stranded loop region present in the intermediate LAMP products. By bringing the two fluorophores in close proximity, energy transfer occurs and a real-time FRET signal is generated during the isothermal amplification reaction. FIG. 1A illustrates a LAMP intermediate product, wherein one loop end has been enlarged to show in detail the hybridization of the oligonucleotides employed in the FRET assay detection step.

Among detection methods based on fluorescence energy transfer, hybridization-induced fluorescence quenching has also been exploited in LAMP applications, particularly through the principle of guanine quenching (Zerilli et al. 2010. Clin Chem 56:1287-96). In such an approach, the fluorescence emitted by a 5' labeled LAMP loop primer is progressively quenched upon hybridization to a complementary target sequence containing a guanine. The extent of the quenching effect depends on the number and positions of the adjacent G bases on the complementary target sequence. As target sequences accumulate in a real-time LAMP assay, quantitative measurements of nucleic acid amplification may be achieved by monitoring the amount of quenched fluorescence as a consequence of the incorporation of the dye-labeled loop primer in the amplification products. Such a strategy, however, suffers of the disadvantage of being dependent on the specific nucleotide sequence of the target nucleic acid and is limited by the presence and/or position of guanine nucleotides within such sequence.

In recent years, large efforts have been directed toward adapting isothermal methods such as LAMP into molecular diagnostic assays, taking advantage of the simplified testing equipment which does not require temperature cycling and allows versions to be produced for use in quite elementary health care settings. As isothermal techniques are being adopted as diagnostic tools, an essential requirement for such techniques is their ability to generate a patient result in a very short time, in order to provide reliable and rapid assistance in clinical decision making for every stage in patient care, i.e. early diagnosis, risk assessment, screening, staging and prognosis, therapy selection and monitoring. For instance, early diagnosis of hematological malignancies such as acute leukemia is crucial to ensure a good prognosis for patients, since a timely treatment may be crucial and decisive in the disease management.

Thus, there exists a need in the art to develop loop-mediated isothermal amplification methods capable of accomplishing a rapid detection of target nucleic acid sequences without affecting critical assay parameters such as specificity, sensitivity and accuracy.

This and other needs are met by the method, set of oligonucleotides and kit as defined in the appended claims, which form an integral part of the description.

SUMMARY OF THE INVENTION

As further illustrated in the experimental section below, the present invention provides a method for the detection of LAMP amplification of target nucleic acid sequences, optionally including the detection of mutations in target nucleic acid sequences, which makes use of the principle of fluorescence energy transfer. The method of the present invention employs a DNA polymerase having strand displacement activity and a set of oligonucleotide LAMP primers consisting of two outer primers, namely F3 and B3, two inner primers, namely FIP and BIP, one or two loop primers, namely LF and/or LB, and one nucleic acid probe. A description of the features and function of the LAMP primers and loop primers is found e.g. at the Eiken web site (loopamp.eiken.co.jp/e/lamp/primer.html; loopamp.eiken-.cojp/e/lamp/loop.html).

BRIEF DESCRIPTION OF THE DRAWINGS

FIG. 1A illustrates a LAMP intermediate product, wherein one loop end has been enlarged to show in detail the hybridization of the oligonucleotides employed in the FRET assay detection step. FIG. 1B illustrates a LAMP intermediate product, wherein one loop end has been enlarged to show in detail the hybridization of the oligonucleotides employed in the FRET assay detection step.

DETAILED DESCRIPTION OF THE INVENTION

According to the present invention, the first inner primer FIP consists of a 3' nucleic acid sequence designated as F2, which is complementary to a F2c region of the target nucleic acid sequence, and a 5' nucleic acid sequence designated as F1c. The second inner primer BIP consists of a 3' nucleic acid sequence designated as B2, which is complementary to a B2c region of the target nucleic acid sequence, and a 5' nucleic acid sequence designated as B1c. The F2c and B2c regions are non overlapping regions located on opposite strands of the target nucleic acid sequence.

The external primer F3 consists in the F3 region that is complementary to the F3c region; the external primer B3 consists in the B3 region that is complementary to the B3c region.

As mentioned above, the method of the present invention employs one or two loop-primers, i.e. a Loop Primer B and/or Loop Primer F (which are designated in the following as "LF loop-primer" and "LB loop-primer", respectively), which contain sequences complementary to the single stranded loop region located between the B1 and B2 regions or located between the F1 and F2 regions.

Typically, when used in a LAMP reaction, loop-primers hybridize to the intermediate LAMP products and provide an increased number of starting points for DNA synthesis. According to the invention, either the LF loop primer or the LB loop-primer, if present, is labeled at its 5'-end with at least one acceptor fluorophore.

Compared with standard LAMP technology, the method of the invention involves the use of an additional oligonucleotide, more particularly a nucleic acid probe, which is labeled at its 3'-end with at least one donor fluorophore. Said nucleic acid probe is capable of hybridizing to the target nucleic acid sequence at a position which is 5' to the labeled LF or LB primer so that, when hybridized to the target nucleic acid sequence, the 3'-end of the nucleic acid probe is brought into close proximity to the 5'-end of the labeled LF or LB loop primer.

In the present description, a nucleic acid sequence (either a primer or a probe) that is capable of hybridizing to a given target nucleic acid sequence is for example complementary to said nucleic acid sequence.

It is noted that a "close proximity" of said labeled loop-primer and said labeled nucleic acid probe occurs only during the amplification phase of a LAMP reaction when the loop-primer is incorporated and extended in the LAMP amplification product.

Figure 1A:
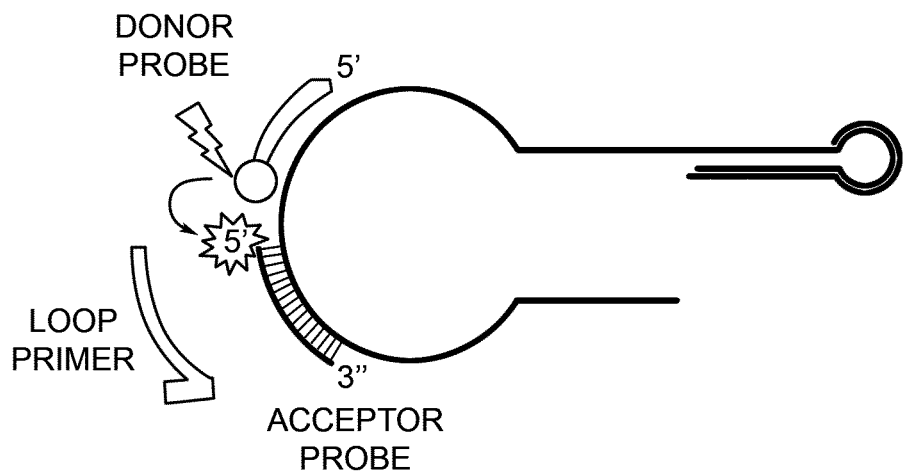
FIGS. 1A-1B.
Figure 1B:
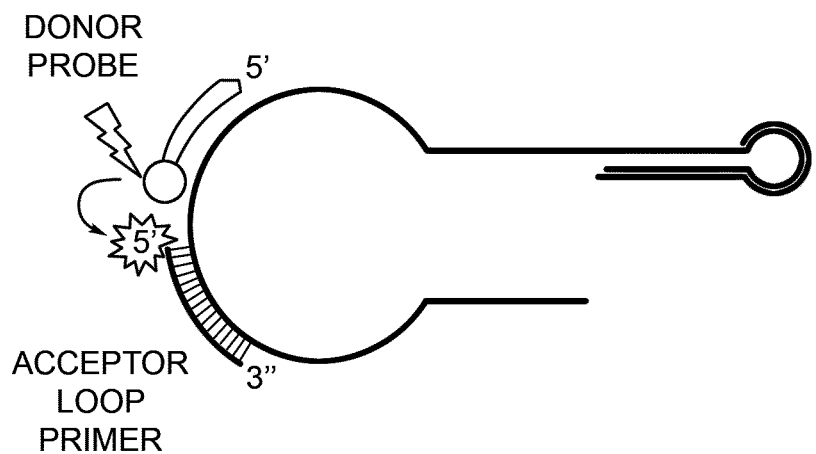

As shown in FIG. 1B, the method according to the invention employs a loop-primer labeled at its 5'-end with at least one acceptor fluorophore in combination with one nucleic acid probe labeled at its 3'-end with at least one donor fluorophore. FIG. 1B illustrates a LAMP intermediate product, wherein one loop end has been enlarged to show in detail the hybridization of the oligonucleotides employed in the FRET assay detection step.

The labeled loop-primer may be either LF or LB (when LB is present). According to the invention, upon hybridization of said oligonucleotides to the target nucleic acid sequence during the LAMP reaction, the donor fluorophore at the 3'-end of the nucleic acid probe is brought into close proximity to the acceptor fluorophore at the 5'-end of the LF or LB loop primer. Fluorescence energy transfer occurs between such fluorophores, e.g. the donor fluorophore located at the 3'-end of the nucleic acid probe transfers excitation energy to the acceptor fluorophore located at the 5'-end of the LF or LB loop primer. As a result, an increase in the intensity of the fluorescence emission of the acceptor fluorophore is generated and detected. Such an increase is an indication of DNA amplification since it is generated upon incorporation of the labeled loop-primer in the LAMP amplification product and subsequent primer extension.

The performance of the method of the invention was evaluated by the present inventors in comparison with prior art fluorescence-based LAMP assays, more specifically the FRET-based LAMP assay described by Chou et al. and the LAMP system making use of intercalating dyes.

In order to compare the performance of the LAMP method of the invention with the assay by Chou et al., a dilution design was used and titration series ranging from $2\times10^1$ copies/µL, to $2\times10^6$ copies/µL, of a denatured plasmid containing a WSSV genomic fragment were subjected to LAMP amplification on a Rotor-Gene Q instrument (Qiagen). In particular, comparative analysis was performed on the dilutions corresponding to $2\times10^3$ copies/4, and $2\times10^6$ copies/µL, respectively. The amplification of the target produced an increasing fluorescent signal with a sigmoidal shape that was detected by setting readings with 1 minute step.

By using the Rotor-Gene Software the normalized signal was generated, and by setting a fluorescence threshold at 0.2 corresponding at around 50% of the fluorescence increment, the Threshold time (minutes) was identified to detect the target amplification.

Figure 2:
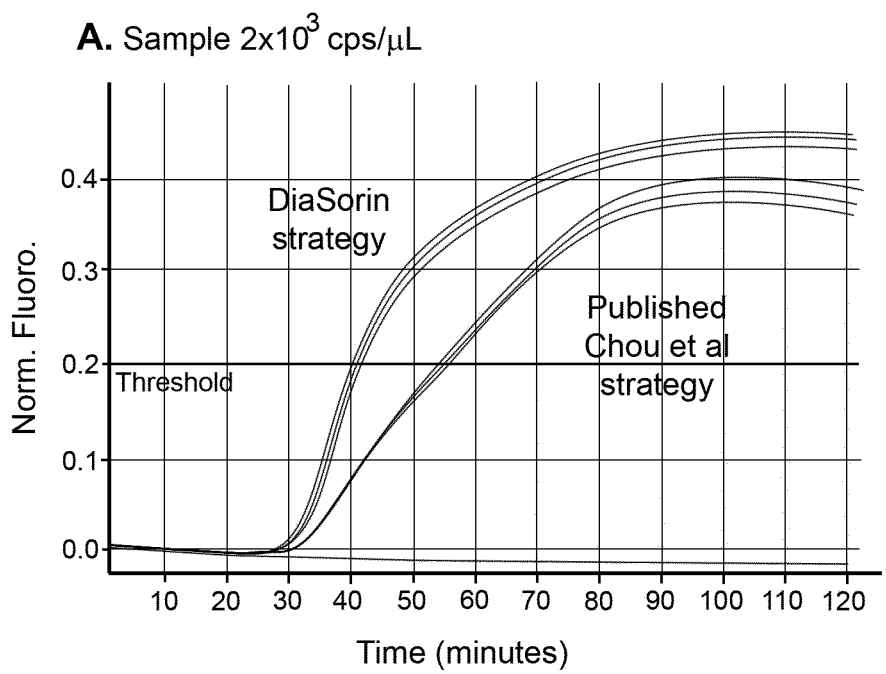
FIG. 2 (Panels A and B) shows a comparative analysis of the threshold time generated for diluted samples (A: $2\times10^3$ cps/µl; B: $2\times10^6$ cps/µl) by the LAMP method of the invention and the LAMP assay by Chou et al.
Figure 2:
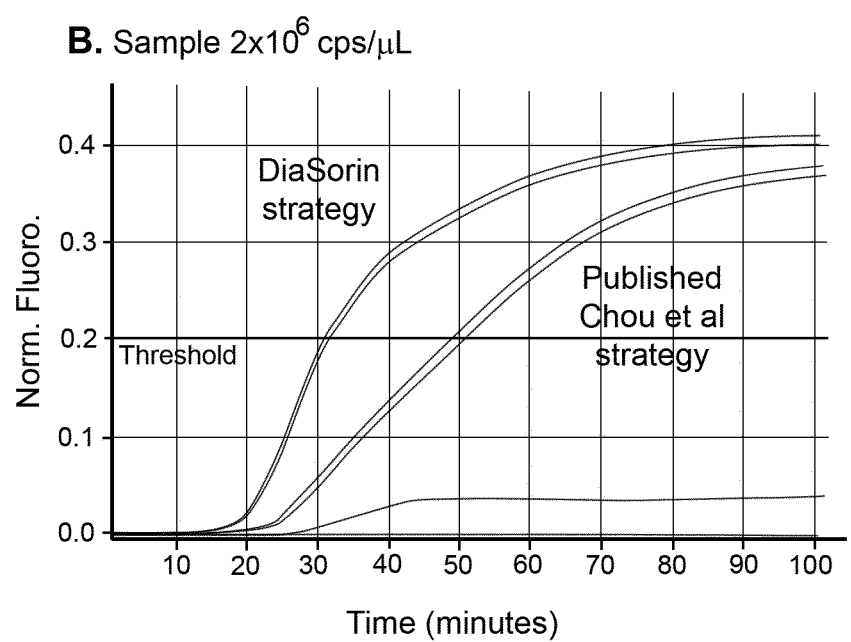

A comparative analysis of the threshold time generated for these diluted samples by each of the LAMP methods under examination showed that the method of the invention achieves a significant earlier detection of the target nucleic acid sequence compared to the method by Chou et al (shown in FIG. 2).

Moreover, the statistical significance of the difference in the detection time measured between the LAMP methods under examination was calculated by performing a Student's t-test, which provided a p-value lower than 0.05.

To further assess the method of the invention for the ability to detect target nucleic acids in a natural matrix, the experimental procedure as above-described was applied to the same dilution of the WSSV plasmid ($2\times10^3$ copies/4, and $2\times10^6$ copies/µL) in human genomic DNA (20 ng/µL). LAMP amplification reactions performed on such dilutions revealed that the presence of material, such a genomic DNA, which may cause interference, did generate delay in the detection of target nucleic acid sequence by both the methods. Moreover, target detection was accomplished by the method of the invention at 10 or more minutes earlier than the detection achieved by the LAMP system by Chou et al.

In assay validation, linearity represents one of the most relevant indicators of assay accuracy, in that it measures the ability of the procedure to return values that are directly proportional to the concentration of the target analyte in the test samples. In the present study, LAMP amplification data obtained by applying either the method of the invention or the method by Chou et al. on the above-indicated sample titration series were subjected to linear regression analysis.

Figure 3:
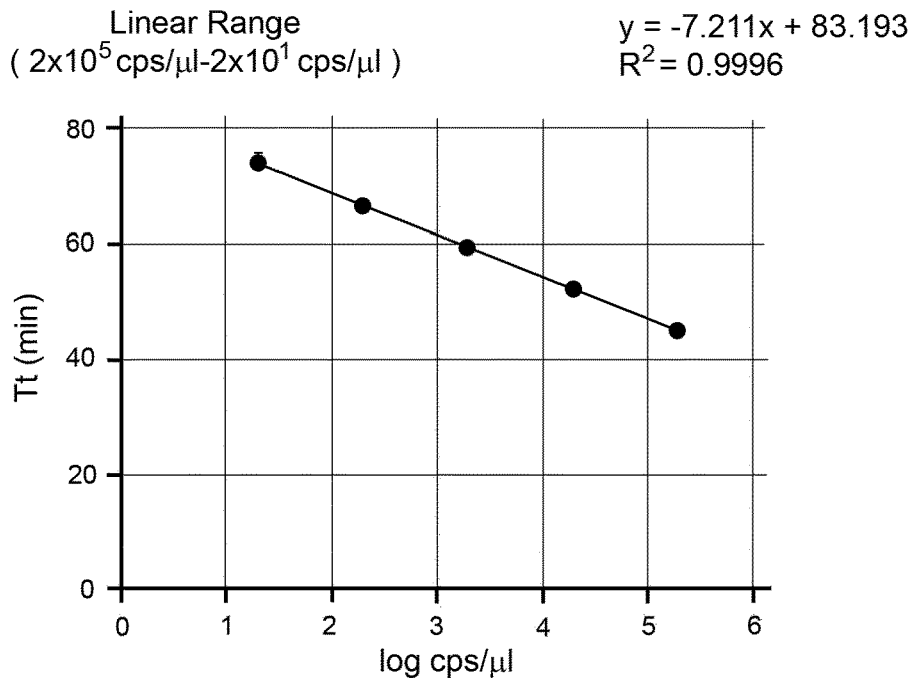
FIG. 3 (Panels A and B) shows the threshold time (indicated in minutes) plotted against the concentration of the plasmid nucleic acid target, expressed as copies/µL, for both (A) the LAMP method of the invention and (B) the LAMP assay by Chou et al.
Figure 3:
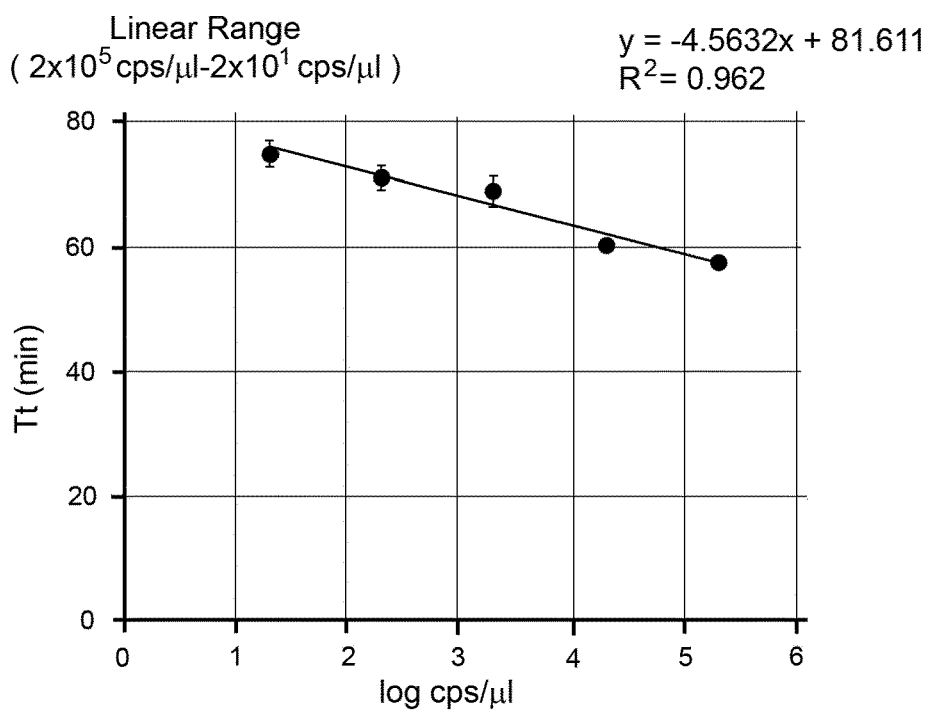

In FIG. 3, the threshold time (indicated in minutes) is plotted against the concentration of the plasmid nucleic acid target, expressed as copies/µL, for both (A) the LAMP method of the invention and (B) the LAMP assay by Chou et al. This figure shows that the method of the present invention provides a superior linearity since a correlation coefficient ($R^2$)=0.99, and a slope=−7.2 were calculated for the regression line. Furthermore, the determination of such a good linearity is indicative of assay precision as well, as it implies high reproducibility among replicate measurements.

Figure 4:
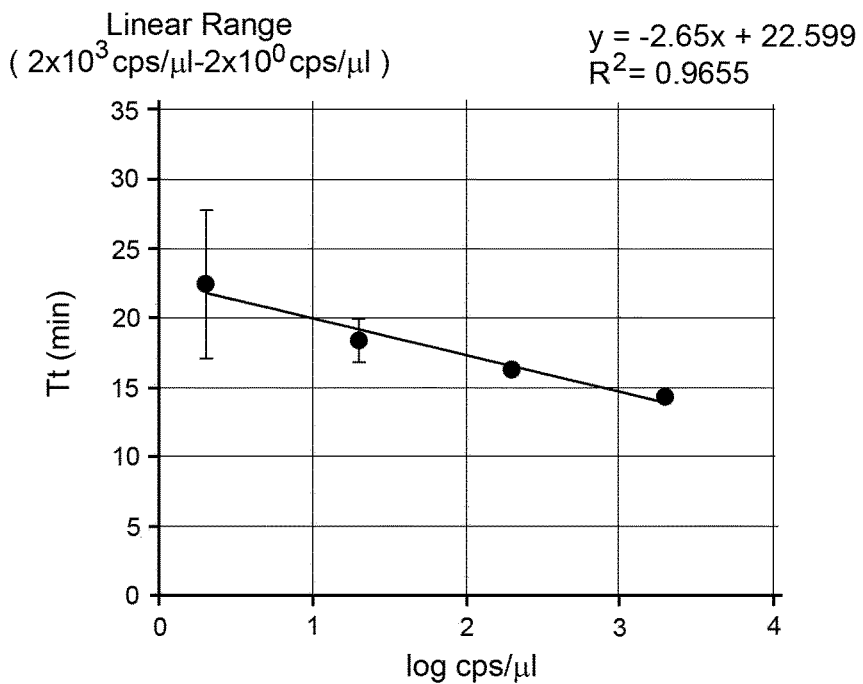
FIG. 4 (Panels A and B) shows the threshold time (indicated in minutes) plotted against the concentration of the plasmid nucleic acid target, expressed as copies/µL, for both (A) the LAMP method of the invention and (B) the intercalating dye assay.
Figure 4:
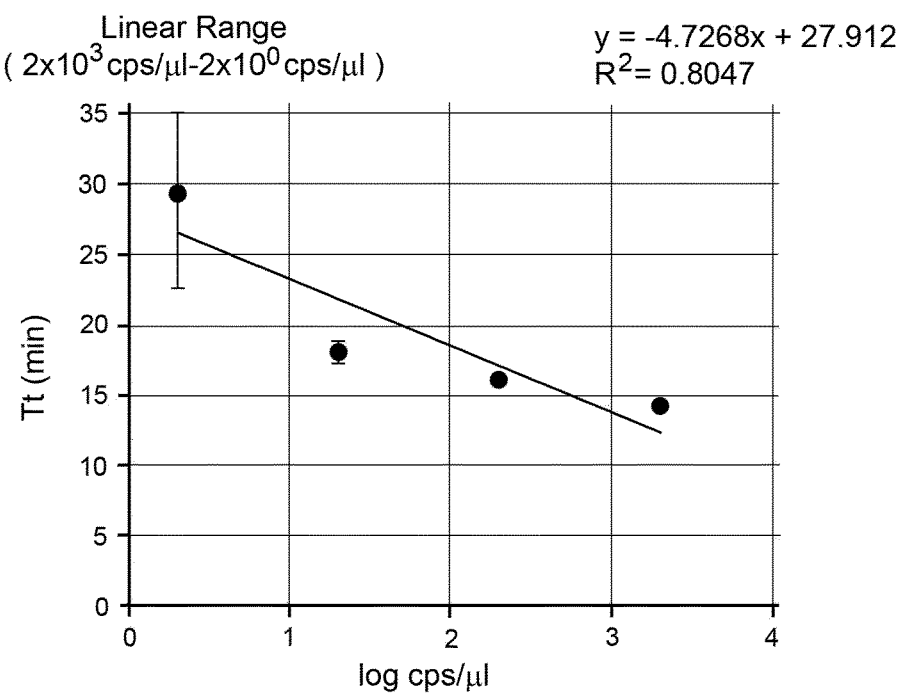

The present inventors performed a further evaluation by comparing the performance of the method of the invention with a LAMP assay that involves the use of intercalating dyes for fluorescence detection. Linear regression analysis was applied on the LAMP amplification data obtained by carrying out either the method of the present invention or the intercalating dye-based assay on ten-fold serially diluted plasmid DNA samples containing the MYH11 gene. The results of linear regression analysis are shown in FIG. 4. This figure shows the threshold time (indicated in minutes) plotted against the concentration of the plasmid nucleic acid target, expressed as copies/µL, for both (A) the LAMP method of the invention and (B) the intercalating dye assay. The data obtained confirm a significant higher linearity of the method of the present invention compared with the LAMP system using the YO-PRO intercalating dye ($R^2$=0.97 versus $R^2$=0.80).

Along with the better assay linearity, a higher analytical sensitivity and wider linearity range were observed for the method of the present invention. Finally, compared to the intercalating dye-based LAMP, the method of the present invention which employs a labeled loop-primer/probe FRET pair results in enhanced assay specificity, since intercalating dyes such as YO-PRO emit a fluorescence signal upon binding to any double-stranded DNA, irrespective of the specific nucleotide sequence.

In the method of the present invention, the amplification of the target nucleic acid sequence leads to a detectable change in a fluorescence parameter, namely an increase in acceptor fluorescence intensity when energy transfer occurs between the donor fluorophore at the 3'-end of the nucleic acid probe and the acceptor fluorophore at the 5'-end of the LF or LB loop primer.

It is to be understood that other fluorescence parameters which are affected by the proximity of the donor and acceptor fluorophores and consequently by the acceptor fluorescence emission may also be evaluated, including, for example, the ratio of donor and/or acceptor fluorescence intensities or fluorescence life-time.

As outlined above, acceptance of donor excitation energy by a FRET acceptor fluorophore requires close proximity between said molecules and the efficiency of FRET is very sensitive to the distance and relative orientation between donor and acceptor. According to the method of the present invention, upon hybridization to the target nucleic acid sequence, the distance between the labeled 3'-end of the nucleic acid probe and the labeled 5'-end of the loop primer should preferably be comprised between zero and 6 nucleotides, for example zero, 1, 2, 3, 4, 5 or 6 nucleotides.

According to the present invention, the nucleic acid probe comprises at least one donor fluorophore linked to its 3'-end. Such a donor fluorophore acts as a blocker of DNA synthesis in that it makes the 3'-terminal of the nucleic acid probe no longer available as origin for DNA polymerization.

Conversely, in the present invention the acceptor fluorophore carried by the labeled loop-primer is linked to the 5'-end of said oligonucleotide in order to avoid any interference with DNA synthesis during LAMP reaction. Specifically, the labeled loop-primer according to the invention has a 3'-free hydroxyl group which serves as origin for the synthesis of the complementary DNA strand.

Since target detection is achieved directly via signal components linked on specific oligonucleotides, the method of the present invention provides a sequence-specific detection technology. According to the invention, the labeled nucleic acid probe and/or labeled loop-primer may be designed to tolerate sequence variations for detection of diverse DNA or RNA sequences or to differentiate between sequence polymorphism. In addition, it is understood that hybridization of the nucleic acid probe or the loop-primer with their respective complementary sequences on the target nucleic acid may be enhanced by incorporating in such oligonucleotides certain types of modified nucleotides, for example, 2'-O-methylribonucleotides or nitropyrole-based nucleotides, or certain types of nucleic acid analogs with non-natural backbone, for example PNA (peptide nucleic acid) or LNA (locked nucleic acid). The use of nucleic acid analogs in nucleic acid amplification methods is well established and known to the person skilled in the art.

In the context of the present invention, the term "target nucleic acid sequence" refers to nucleic acid sequences to be amplified and detected. This also includes the complementary second strand of the nucleic acid sequences to be amplified and either strand of a copy of the nucleic acid sequence which is produced by amplification. The target nucleic acid can originate from a variety of sources. For example, target nucleic acids can be naturally occurring DNA or RNA isolated from any source, recombinant molecules, cDNA, or synthetic analogs, as known in the art. In some embodiments, the target nucleic acid sequence may comprise one or more single-nucleotide polymorphisms (SNPs), allelic variants, and other mutations such as deletion mutations, insertion mutations, point mutations. In other embodiments, the target nucleic acid sequence may comprise a junction sequence of a fusion gene, possibly associated with cancer. In yet another embodiment, the target nucleic acid sequence may originate from a microorganism, including specific clones or strains of microorganisms, possibly involved in inducing diseases in human beings and animals.

The method of the present invention is also suitable for quantitatively determine the amount of target nucleic acid sequences in a sample. In a preferred embodiment of the invention, the quantification of a target nucleic acid sequence is accomplished via the generation of a standard curve by plotting a graph of known copy number (or concentration) of such target nucleic acid sequence against LAMP assay time to positivity. Quantification of unknown target copy number (or concentration) in the test samples may be extrapolated from the standard curve on the basis of the time to positivity measured in the unknown sample.

Another aspect of the present invention is a set of oligonucleotides for detecting loop-mediated isothermal amplification (LAMP) of a target nucleic acid sequence, the set consisting of a first outer primer F3, a second outer primer B3, a first inner primer FIP, a second inner primer BIP, a first loop-primer LF, a second loop-primer LB and one nucleic acid probe, all as defined above with reference to the method of the invention.

Either the LF loop primer or the LB loop primer (when LB is present) is labeled at its 5'-end with at least one acceptor fluorophore and the nucleic acid probe is labeled at its 3'-end with at least one donor fluorophore.

A requirement for Förster resonance energy transfer to occur is that the emission spectrum of the donor fluorophore overlaps with the absorption spectrum of the acceptor fluorophore, so that excitation by lower-wavelength light of the donor fluorophore is followed by transfer of the excitation energy to the acceptor fluorophore.

There are many molecules which may serve either as the donor or the acceptor fluorophore in the present invention.

According to a preferred embodiment, the donor fluorophore is selected from the group consisting of Fluorescein, BODIPY FL, Alexa555, ATTO550, Cy3, FAM, TET, HEX, JOE, VIC, Cy3, NED, Quasar 570, Oyster 556, TAMRA and/or the acceptor fluorophore is selected from the group consisting of Cy5.5, Cy5, ATTO647N, Alexa 647, ROX, LC red 610, Texas red, LC red 640, LC red 670, Quasar 670, Oyster 645, LC red 705.

Especially preferred is the donor/acceptor pair BODIPY FL/ATTO647N.

In yet another embodiment, the nucleic acid probe and/or the loop primer are labeled with more than one fluorophore, preferably two fluorophores.

In the most preferred embodiment, the FRET donor/acceptor pair consists of two BODIPY FL fluorophore and one ATTO647N fluorophore, respectively. The selection of suitable donor/acceptor fluorophore pair suitable for the present invention is well within the knowledge of the person skilled in the art.

As mentioned above, a further aspect of the present invention is a kit for detecting loop-mediated isothermal amplification (LAMP) of a target nucleic sequence, the kit comprising the set of oligonucleotides as defined above, as well as one or more DNA polymerases having strand displacement activity. The DNA polymerase is preferably selected from the group consisting of Bst large fragment polymerase, Bst 2.0, Bst 3.0, Bca (exo-), Vent, Vent (exo-), Deep Vent, Deep Vent (exo-), Φ29 phage, MS-2 phage, Z-Taq, KOD, Klenow fragment, GspSSD, GspF, OmniAmp Polimerase, SD Polimerase and any combination thereof. The most preferred DNA polymerase is the Bst large fragment polymerase.

The following experimental section is provided purely by way of illustration and is not intended to limit the scope of the invention as defined in the appended claims.

EXAMPLES

Example 1—Comparison of the LAMP Method of the Invention with the LAMP Assay by Chou et al Sample Preparation To compare the LAMP method of the invention with the LAMP assay described in Chou et al., a suitable target nucleic acid sequence was prepared. Briefly, a 350-bp DNA fragment derived from the White spot syndrome virus (WSSV) genome (nt226681-227934, GenBank AF332093.1) was cloned into the pMA-T vector (GE-NEART) by using the Sfi I/Sfi I restriction site combination to provide the positive control. Ten-fold dilution series in the range of approximately $2\times10^6$ copies/µL to $2\times10^1$ copies/µL were prepared for the recombinant WSSV plasmid.

Two different plasmid dilution series were prepared using as diluent either Tris-HCl 10 mM, pH 8.5 alone, or this buffer additionally containing human genomic DNA (20 ng/µl).

In the present study, the analyzed plasmid dilutions were denatured at 100° C. for 10 minutes. After denaturation, the plasmid samples were immediately placed on ice for 10 minutes.

LAMP Reaction

The LAMP oligonucleotide primers and probes employed for the comparative analysis were designed as described in Chou et al., and are listed in Table 1 below.

TABLE 1

| Oligo name | Sequence (5' -> 3') | SEQ ID NO: |
|---|---|---|
| F3 | TGATTCAGATGGCATGGATACTT (Forward outer primer) | 1 |
| B3 | CCGATACTGCCATTGAAAGC (Reverse outer primer) | 2 |
| FIP | TGTTATGGTAGTGAACCCCTTTGCACGACTTATCATTCAAGACATCAAT (Forward inner primer) | 3 |

TABLE 1-continued

| Oligo name | Sequence (5' -> 3') | SEQ ID NO: |
|---|---|---|
| BIP | GGAAGAAAGATACAAGCCCATTGGCGCTCCCTTACCACCTTCCTTAATC (Reverse inner primer) | 4 |
| LoopB | GCCATTGAAGCAGTGTTGGGAT (Reverse loop) | 5 |
| LoopF | GATCGTTAACAACAACAATACTGGA (Forward loop) | 6 |
| LCF | CACCCACAGCGGCTCTTGC-Fluorescein (3'fluorescein labeled FRET probe) | 7 |
| LCQ | LC640-CGTTCGCCATTGAAGCAGTGTTGG-Phosphate (5'LC640 labeled FRET probe) | 8 |

Table 1 contains the full set of oligonucleotides used in the assay by Chou et al. The set of oligonucleotides employed in the LAMP method according to the invention differs from the oligonucleotide set by Chou et al. for the following features:

1) it contains one single nucleic acid probe, namely LCF, which is labeled at its 3'-end with fluorescein;

2) it does not include any loop primer LoopB, and the latter is replaced with the LCQ primer, which is labeled at its 5'-end with the fluorescent moiety LC640. In the light of the above, the method by Chou et al. provides for the generation of a fluorescent amplification signal by means of the FRET mechanism between a labeled donor probe and a labeled acceptor probe. Conversely, in the method according to the present invention the function of acceptor oligonucleotide is carried out by one of the loop primers, previously labeled, thereby reducing the number of oligonucleotides employed in the LAMP reaction. Moreover, the method of the invention overcomes the disadvantage associated with the assay by Chou et al. of a possible competition of the FRET probes employed in said assay with the loop primers for the binding to the same target nucleotide sequence.

In the present study, the following primer concentrations were used in the LAMP reactions: 0.375 µM outer primers (F3 and B3), 2 µM inner primers (FIP and BIP), 1.1 µM loop primer LoopF, 0.3 µM loop primer LoopB (present only in the reaction according to Chou et al), 0.25 µM LCF and LCQ.

The LAMP reactions were performed in a 20 µl mixture containing: 0.375 mM dNTPs, 2.4 U of Bst DNA polymerase Large Fragment (New England BioLabs, Beverly, MA, USA), 1× Reaction Buffer (20 mM HEPES buffer, pH 7.9, 20 mM KCl, 3 mM MgCl2, and 0.1% Triton X100).

The reaction mixtures were incubated at 60° C. for 120 minutes on a Rotor-Gene Q instrument (Qiagen). The amplification products were then kept at 4° C.

LAMP amplification of the recombinant WSSV plasmid was detected by the analysis of the normalized fluorescent signal generated during the reaction. The Threshold time was identified by setting a fluorescence threshold at 0.2, corresponding at around 50% of the fluorescence increment.

Data Analysis and Normalization

Data analysis was performed using the statistical package within the Microsoft Excel. The same package was used for linear regression analysis.

Data normalization was obtained by means of the Rotor-Gene Pure Detection v2.1 Software.

Example 2—Comparison of the LAMP Method of the Invention with an Intercalating Dye-Based LAMP Assay Sample Preparation In order to compare the performance of the method of the invention with a LAMP assay that involves the use of intercalating dyes, a suitable target nucleic acid sequence was prepared. Briefly, a 350-bp DNA fragment derived from the MYH11 gene (GenBank D10667.1) was cloned into the pMA-T vector (GENEART) by using the Sfi I/Sfi I restriction site combination to provide the positive control.

The recombinant MYH11 plasmid was serially diluted 10-fold in buffer Tris-HCl 10 mM, pH 8.5, from approximately $2\times10^6$ copies/µL to $2\times10^1$ copies/µL.

In the present study, the analyzed plasmid dilutions were denatured at 100° C. for 10 minutes. After denaturation, the plasmid samples were immediately placed on ice for 10 minutes.

LAMP Reaction

In Table 2 below are listed the LAMP oligonucleotide primers and probes employed for the comparative analysis.

TABLE 2

| Oligo name | Sequence (5' -> 3') | SEQ ID NO: |
|---|---|---|
| F3 | TCAAGAAACTGGAGGATGAG (Forward outer primer) | 9 |
| B3 | TTCCGTTTCAGCTTCTCC (Reverse outer primer) | 10 |
| FIP | TGTCGTTAAGTCACTAATCCTC TGGTCATGGATGATCAGA (Forward inner primer) | 11 |
| BIP | GCCAAGAATCTTACCAAGCTG AAGGCTCTTCTCTTCC (Reverse inner primer) | 12 |

TABLE 2-continued

| Oligo name | Sequence (5' -> 3') | SEQ ID NO: |
|---|---|---|
| Donor Probe | GAATCTATGATTTCAG-Bodipy FL (3' Bodipy FL-labeled FRET probe) | 13 |
| Acceptor LB loop | ATTO 647N-ACTGGAAGTGCGGCTAAAG (Reverse 5' ATTO647N labeled loop) | 14 |

In the LAMP reaction according to the method of the invention, the following oligonucleotide concentrations were used: 0.05 µM outer primers (F3 and B3), 0.4 µM inner primers (FIP and BIP), 0.2 µM Acceptor LB loop primer and 0.2 µM Donor FRET probe. Conversely, besides the above-indicated outer and inner primers, the oligonucleotides set employed in the intercalating dye-based LAMP assay included only the LB loop primer in non-labeled form.

The LAMP reactions were performed in a 25 µl mixture containing: 1.4 mM dNTPs, 8 U of Bst DNA polymerase Large Fragment (New England BioLabs, Beverly, MA, USA), 8 mM MgCl2, 1× Reaction Buffer (30 mM Tris-HCl, pH 8.0, 30 mM KCl, and 0.1% Triton X100).

The reaction mixtures set up for the intercalating dye-based LAMP assay further included the YO-PRO intercalating dye (Life Technologies) at the concentration of 1 µM.

The LAMP amplification reaction was conducted at 65° C. for 40 minutes on a Rotor-Gene Q instrument (Qiagen). The amplification products were then kept at 4° C.

LAMP amplification of the recombinant MYH11 plasmid was detected by the analysis of the normalized fluorescent signal generated during the reaction. The Threshold time was identified by setting a fluorescence threshold at 0.2, corresponding at around 50% of the fluorescence increment.

Data Analysis and Normalization

Data analysis was performed using the statistical package within the Microsoft Excel. The same package was used for linear regression analysis.

Data normalization was obtained by means of the Rotor-Gene Pure Detection v2.1 Software.

What is claimed is:

1. A set of oligonucleotides for detecting loop-mediated isothermal amplification (LAMP) of a target nucleic acid sequence, the set comprising:
    (a) a first outer primer F3 and a second outer primer B3;
    (b) a first inner primer FIP and a second inner primer BIP, wherein:
        (1) FIP consists of a 3' nucleic acid sequence F2 and a 5' nucleic acid sequence F1c and BIP consists of a 3' nucleic acid sequence B2 and a 5' nucleic acid sequence B1c;
        (2) F2 is complementary to a F2c region of the target nucleic acid sequence and B2 is complementary to a B2c region of the target nucleic acid sequence; and
        (3) F2c and B2c are non-overlapping regions located on opposite strands of the target nucleic acid sequence;
    (c) a loop primer LF and/or a loop primer LB, wherein:
        (1) said loop primer LF is capable of hybridizing to a region of the target nucleic acid sequence between F2 and F1; and
        (2) said loop primer LB is complementary to a region of the target nucleic acid sequence between B1 and B2;
        wherein said loop primer LF, or said loop primer LB, if present, is labeled with at least one acceptor fluorophore at its 5'-end; and
    (d) a nucleic acid probe, labeled at its 3'-end with at least one donor fluorophore capable of transferring excitation energy to said at least one acceptor fluorophore of a labeled loop primer, wherein:
        (1) if said loop primer LF is labeled with said at least one acceptor fluorophore at its 5'-end, the nucleotide sequence of said nucleic acid probe is selected so that said nucleic acid probe is capable of hybridizing to the target nucleic acid sequence at a position 5' to the position at which such labeled loop primer LF hybridizes to said target nucleic acid sequence; and
(2) if said loop primer LB is labeled with said at least one acceptor fluorophore at its 5'-end, the nucleotide sequence of said nucleic acid probe is selected so that said nucleic acid probe is capable of hybridizing to the target nucleic acid sequence at a position 5' to the position at which such labeled loop primer LB hybridizes to said target nucleic acid sequence;
wherein hybridization of said nucleic acid probe to the target nucleic acid sequence causes the 3'-end of the nucleic acid probe to be in close proximity to the 5'-end of hybridized labeled loop primer, and wherein:
(i) the intensity of fluorescence emission of the acceptor fluorophore increases upon absorption of the donor fluorophore excitation energy;
(ii) the ratio of donor and/or acceptor fluorescence intensities of fluorescence changes upon absorption of the donor fluorophore excitation energy; or
(iii) the fluorescence life-time of the acceptor fluorophore changes upon absorption of the donor fluorophore excitation energy.

2. The set of oligonucleotides according to claim 1, wherein said set of oligonucleotides includes said labeled loop primer LF, and does not include said loop primer LB.

3. The set of oligonucleotides according to claim 1, wherein said set of oligonucleotides includes said labeled loop primer LB, and does not include said loop primer LF.

4. The set of oligonucleotides according to claim 1, wherein said set of oligonucleotides includes said labeled loop primer LB, and additionally includes loop primer LF.

5. The set of oligonucleotides according to claim 4, wherein both said loop primer LB and said loop primer LF are labeled.

6. The set of oligonucleotides according to claim 1, wherein said nucleic acid probe is labeled at its 3'-end with at least one donor fluorophore selected from the group consisting of Fluorescein, BODIPY FL, Alexa555, ATTO550, Cy3, FAM, TET, HEX, JOE, VIC, Cy3, NED, Quasar 570, Oyster 556, and TAMRA.

7. The set of oligonucleotides according to claim 6, wherein said nucleic acid probe is labeled at its 3'-end with BODIPY FL.

8. The set of oligonucleotides according to claim 1, wherein said labeled loop primer is labeled at its 5'-end with at least one acceptor fluorophore selected from the group consisting of Cy5.5, Cy5, ATTO647N, Alexa 647, ROX, LC red 610, Texas red, LC red 640, LC red 670, Quasar 670, Oyster 645, and LC red 705.

9. The set of oligonucleotides according to claim 8, wherein said labeled loop primer is labeled at its 5'-end with ATTO647N.

10. The set of oligonucleotides according to claim 1, wherein said nucleic acid probe is labeled at its 3'-end with BODIPY FL, and said labeled loop primer is labeled at its 5'-end with ATTO647N.

11. A kit for detecting loop-mediated isothermal amplification (LAMP) of a target nucleic acid sequence, the kit comprising the set of oligonucleotides according to claim 1 and a DNA polymerase having strand displacement activity.

12. The kit according to claim 11, wherein said set of oligonucleotides includes said labeled loop primer LF, and does not include said loop primer LB.

13. The kit according to claim 11, wherein said set of oligonucleotides includes said labeled loop primer LB, and does not include said loop primer LF.

14. The kit according to claim 11, wherein said set of oligonucleotides includes said labeled loop primer LB, and additionally includes loop primer LF.

15. The kit according to claim 14, wherein both said loop primer LB and said loop primer LF are labeled.

16. The kit according to claim 11, wherein said nucleic acid probe is labeled at its 3'-end with at least one donor fluorophore selected from the group consisting of Fluorescein, BODIPY FL, Alexa555, ATTO550, Cy3, FAM, TET, HEX, JOE, VIC, Cy3, NED, Quasar 570, Oyster 556, and TAMRA.

17. The kit according to claim 11, wherein said labeled loop primer is labeled at its 5'-end with at least one acceptor fluorophore selected from the group consisting of Cy5.5, Cy5, ATTO647N, Alexa 647, ROX, LC red 610, Texas red, LC red 640, LC red 670, Quasar 670, Oyster 645, and LC red 705.

18. The kit according to claim 15, wherein:
(a) said nucleic acid probe is labeled at its 3'-end with BODIPY FL; and/or
(b) said labeled loop primer is labeled at its 5'-end with ATTO647N.

19. The kit according to claim 11, wherein said kit additionally comprises deoxynucleotide triphosphates sufficient to permit primer extension to occur.

20. The kit according to claim 11, wherein the DNA polymerase is selected from the group consisting of Bst large fragment polymerase, Bst 2.0, Bst 3.0, Bca (exo-), Vent, Vent (exo-), Deep Vent, Deep Vent (exo-), Φ29 phage, MS-2 phage, Z-Taq, KOD, Klenow fragment, GspSSD, GspF, OmniAmp Polimerase, SD Polimerase and any combination thereof.

* * * * *

SEQUENCE LISTING

<160> NUMBER OF SEQ ID NOS: 14

<210> SEQ ID NO 1
<211> LENGTH: 23
<212> TYPE: DNA
<213> ORGANISM: artificial sequence
<220> FEATURE:
<223> OTHER INFORMATION: Forward outer primer

<400> SEQUENCE: 1
tgattcagat ggcatggata ctt                                    23

<210> SEQ ID NO 2
<211> LENGTH: 20
<212> TYPE: DNA
<213> ORGANISM: artificial sequence
<220> FEATURE:
<223> OTHER INFORMATION: Reverse outer primer

<400> SEQUENCE: 2
ccgatactgc cattgaaagc                                        20

<210> SEQ ID NO 3
<211> LENGTH: 49
<212> TYPE: DNA
<213> ORGANISM: artificial sequence

```
<220> FEATURE:
<223> OTHER INFORMATION: Forward inner primer

<400> SEQUENCE: 3
tgttatggta gtgaacccct ttgcacgact tatcattcaa gacatcaat            49

<210> SEQ ID NO 4
<211> LENGTH: 49
<212> TYPE: DNA
<213> ORGANISM: artificial sequence
<220> FEATURE:
<223> OTHER INFORMATION: Reverse inner primer

<400> SEQUENCE: 4
ggaagaaaga tacaagccca ttggcgctcc cttaccacct tccttaatc            49

<210> SEQ ID NO 5
<211> LENGTH: 22
<212> TYPE: DNA
<213> ORGANISM: artificial sequence
<220> FEATURE:
<223> OTHER INFORMATION: Reverse loop primer

<400> SEQUENCE: 5
gccattgaag cagtgttggg at                                         22

<210> SEQ ID NO 6
<211> LENGTH: 25
<212> TYPE: DNA
<213> ORGANISM: artificial sequence
<220> FEATURE:
<223> OTHER INFORMATION: Forward loop primer

<400> SEQUENCE: 6
gatcgttaac aacaacaata ctgga                                      25

<210> SEQ ID NO 7
<211> LENGTH: 19
<212> TYPE: DNA
<213> ORGANISM: artificial sequence
<220> FEATURE:
<223> OTHER INFORMATION: 3' fluoresceine labeled FRET probe

<400> SEQUENCE: 7
cacccacagc ggctcttgc                                             19

<210> SEQ ID NO 8
<211> LENGTH: 24
<212> TYPE: DNA
<213> ORGANISM: artificial sequence
<220> FEATURE:
<223> OTHER INFORMATION: 5' LC640 labeled FRET probe

<400> SEQUENCE: 8
cgttcgccat tgaagcagtg ttgg                                       24

<210> SEQ ID NO 9
<211> LENGTH: 20
<212> TYPE: DNA
<213> ORGANISM: artificial sequence
<220> FEATURE:
<223> OTHER INFORMATION: Forward outer primer

<400> SEQUENCE: 9
tcaagaaact ggaggatgag                                            20
```

```
<210> SEQ ID NO 10
<211> LENGTH: 18
<212> TYPE: DNA
<213> ORGANISM: artificial sequence
<220> FEATURE:
<223> OTHER INFORMATION: Reverse outer primer

<400> SEQUENCE: 10
ttccgtttca gcttctcc                                                 18

<210> SEQ ID NO 11
<211> LENGTH: 40
<212> TYPE: DNA
<213> ORGANISM: artificial sequence
<220> FEATURE:
<223> OTHER INFORMATION: Forward inner primer

<400> SEQUENCE: 11
tgtcgttaag tcactaatcc tctggtcatg gatgatcaga                         40

<210> SEQ ID NO 12
<211> LENGTH: 37
<212> TYPE: DNA
<213> ORGANISM: artificial sequence
<220> FEATURE:
<223> OTHER INFORMATION: Reverse inner primer

<400> SEQUENCE: 12
gccaagaatc ttaccaagct gaaggctctt ctcttcc                            37

<210> SEQ ID NO 13
<211> LENGTH: 16
<212> TYPE: DNA
<213> ORGANISM: artificial sequence
<220> FEATURE:
<223> OTHER INFORMATION: 3' Bodipy FL-labeled FRET probe

<400> SEQUENCE: 13
gaatctatga tttcag                                                   16

<210> SEQ ID NO 14
<211> LENGTH: 19
<212> TYPE: DNA
<213> ORGANISM: artificial sequence
<220> FEATURE:
<223> OTHER INFORMATION: Reverse 5' ATTO647N labeled loop

<400> SEQUENCE: 14
actggaagtg cggctaaag                                                19
```